United States Patent
Calvert

(10) Patent No.: US 10,518,045 B2
(45) Date of Patent: Dec. 31, 2019

(54) NEEDLE ASSEMBLIES

(71) Applicant: Owen Mumford Limited, Oxford (GB)

(72) Inventor: Jack Calvert, Oxford (GB)

(73) Assignee: Owen Mumford Limited, Oxford (GB)

( * ) Notice: Subject to any disclaimer, the term of this patent is extended or adjusted under 35 U.S.C. 154(b) by 174 days.

(21) Appl. No.: 15/506,589

(22) PCT Filed: Dec. 3, 2015

(86) PCT No.: PCT/GB2015/053711
§ 371 (c)(1),
(2) Date: Feb. 24, 2017

(87) PCT Pub. No.: WO2016/087870
PCT Pub. Date: Jun. 9, 2016

(65) Prior Publication Data
US 2018/0221591 A1    Aug. 9, 2018

(30) Foreign Application Priority Data
Dec. 4, 2014  (GB) .................................. 1421586.7

(51) Int. Cl.
*A61M 5/32* (2006.01)
*A61M 5/24* (2006.01)

(52) U.S. Cl.
CPC ............ *A61M 5/3271* (2013.01); *A61M 5/32* (2013.01); *A61M 5/321* (2013.01);
(Continued)

(58) Field of Classification Search
CPC .... A61M 2005/3267; A61M 2205/582; A61M 2205/586; A61M 5/2466; A61M 5/3202;
(Continued)

(56) References Cited

U.S. PATENT DOCUMENTS

| 4,946,447 A | 8/1990 | Hardcastle et al. |
| 5,215,534 A | 6/1993 | DeHarde et al. |

(Continued)

FOREIGN PATENT DOCUMENTS

| DE | 19543313 A1 | 6/1997 |
| EP | 0467703 A1 | 1/1992 |

(Continued)

OTHER PUBLICATIONS

International Search report and Written Opinion issued in corresponding PCT Application No. PCT/GB2015/053711, dated Mar. 5, 2016, 3 pages.
(Continued)

*Primary Examiner* — Rebecca E Eisenberg
(74) *Attorney, Agent, or Firm* — Quarles & Brady LLP

(57) ABSTRACT

A needle assembly (1) for mounting on an injection device is disclosed comprising: a main body (10) which is removably attached to an injection device in use; a needle (90) secured in the main body and having a forward portion which projects forwardly from the main body. The needle assembly further includes a shield (50) which is slideably mounted within the main body (10) and an actuator portion (70) which extends outside the main body and is configured for pushing the shield (50) forward manually in use. The shield (50) is slideably moveable between a first position in which the forward portion of the needle (90) projects forwardly of a shield cavity (64), and a second position in which said forward portion of the needle is located within the shield cavity (64). The shield (50) and main body (10) are provided with cooperating features comprising at least one latching element (66) provided on one of the shield (50) or the main body (10) and at least one corresponding engagement feature (44) provided on the other of the shield (50) and the main body. The latching element (66) moves
(Continued)

into a latched position as the shield (50) moves into the second position to hold the shield in its second position.

13 Claims, 5 Drawing Sheets

(52) U.S. Cl.
CPC ........ *A61M 5/3202* (2013.01); *A61M 5/3204* (2013.01); *A61M 5/3213* (2013.01); *A61M 5/2466* (2013.01); *A61M 2005/3267* (2013.01); *A61M 2205/581* (2013.01); *A61M 2205/582* (2013.01); *A61M 2205/586* (2013.01)

(58) Field of Classification Search
CPC .. A61M 5/3204; A61M 5/321; A61M 5/3213; A61M 5/3271
See application file for complete search history.

(56) References Cited

U.S. PATENT DOCUMENTS

| | | | |
|---|---|---|---|
| 5,304,149 | A | 4/1994 | Morigi |
| 5,312,372 | A | 5/1994 | DeHarde et al. |
| 5,342,320 | A | 8/1994 | Cameron |
| 5,466,223 | A | 11/1995 | Bressler et al. |
| 5,486,164 | A | 1/1996 | Streck |
| 5,688,249 | A | 11/1997 | Chang et al. |
| 5,697,908 | A | 12/1997 | Imbert et al. |
| 5,976,111 | A | 11/1999 | Hart |
| 6,004,296 | A | 12/1999 | Jansen et al. |
| 6,149,629 | A | 11/2000 | Wilson et al. |
| 6,183,445 | B1 | 2/2001 | Lund et al. |
| 6,193,696 | B1 | 2/2001 | Jansen et al. |
| 6,623,461 | B1 | 9/2003 | Wilkinson et al. |
| 6,638,256 | B2 | 10/2003 | Jansen et al. |
| 6,855,127 | B2 | 2/2005 | Nakagami et al. |
| 6,860,872 | B2 | 3/2005 | Teichert |
| 6,974,444 | B2 | 12/2005 | Von Teichert |
| 7,060,055 | B2 | 6/2006 | Wilkinson et al. |
| 8,486,016 | B2 | 7/2013 | Kanbar et al. |
| 8,551,051 | B2 | 10/2013 | Salto et al. |
| 2001/0004685 | A1 | 6/2001 | Jansen et al. |
| 2002/0099341 | A1 | 7/2002 | Nakagami et al. |
| 2003/0036730 | A1 | 2/2003 | Von Teichert |
| 2003/0176842 | A1 | 9/2003 | Wilkinson et al. |
| 2003/0229316 | A1 | 12/2003 | Hwang et al. |
| 2004/0024370 | A1 | 2/2004 | Wilkinson et al. |
| 2004/0186440 | A1 | 9/2004 | Jansen et al. |
| 2005/0131348 | A1 | 6/2005 | Von Teichert |
| 2005/0143692 | A1 | 6/2005 | Von Teichert |
| 2005/0143693 | A1 | 6/2005 | Von Teichert |
| 2007/0016141 | A1 | 1/2007 | Salto et al. |
| 2008/0086108 | A1 | 4/2008 | Falkel et al. |
| 2009/0062744 | A1 | 3/2009 | Weilbacher |
| 2009/0131876 | A1 | 5/2009 | Coyne |
| 2011/0160675 | A1 | 6/2011 | Ruan et al. |
| 2011/0208126 | A1 | 8/2011 | Riemelmoser |
| 2012/0130277 | A1 | 5/2012 | Shapland |
| 2013/0123698 | A1 | 5/2013 | Kanbar et al. |
| 2014/0074040 | A1 | 3/2014 | Salto et al. |
| 2014/0107577 | A1 | 4/2014 | Boyd et al. |

FOREIGN PATENT DOCUMENTS

| | | |
|---|---|---|
| EP | 0549382 B1 | 1/1996 |
| EP | 0573947 B1 | 1/1997 |
| EP | 0941134 B1 | 6/2003 |
| EP | 1350529 A1 | 10/2003 |
| EP | 0832659 B1 | 12/2003 |
| EP | 1352668 B1 | 1/2007 |
| EP | 1937335 A1 | 7/2008 |
| EP | 2344223 A1 | 7/2011 |
| WO | 02/20074 | 3/2002 |
| WO | 2008/028304 | 3/2008 |
| WO | 2008045369 A2 | 4/2008 |
| WO | 2008/077706 | 7/2008 |
| WO | 2012166527 A2 | 12/2012 |

OTHER PUBLICATIONS

United Kingdom Search Report issued in corresponding United Kingdom Patent Application No. 1421586.7, dated Jan. 22, 2015, 3 pages.

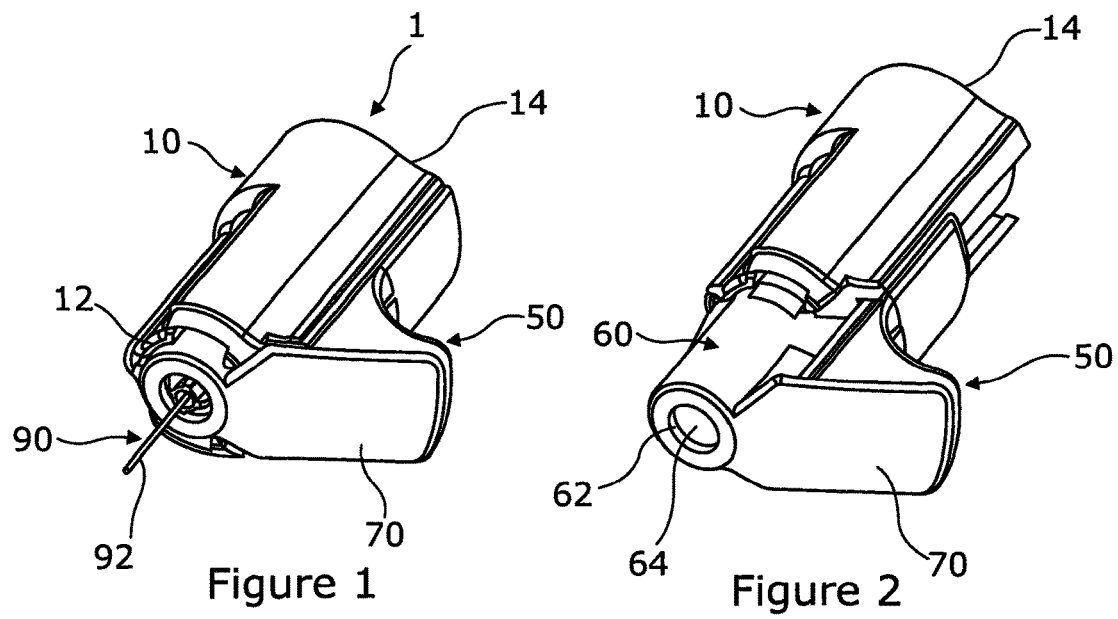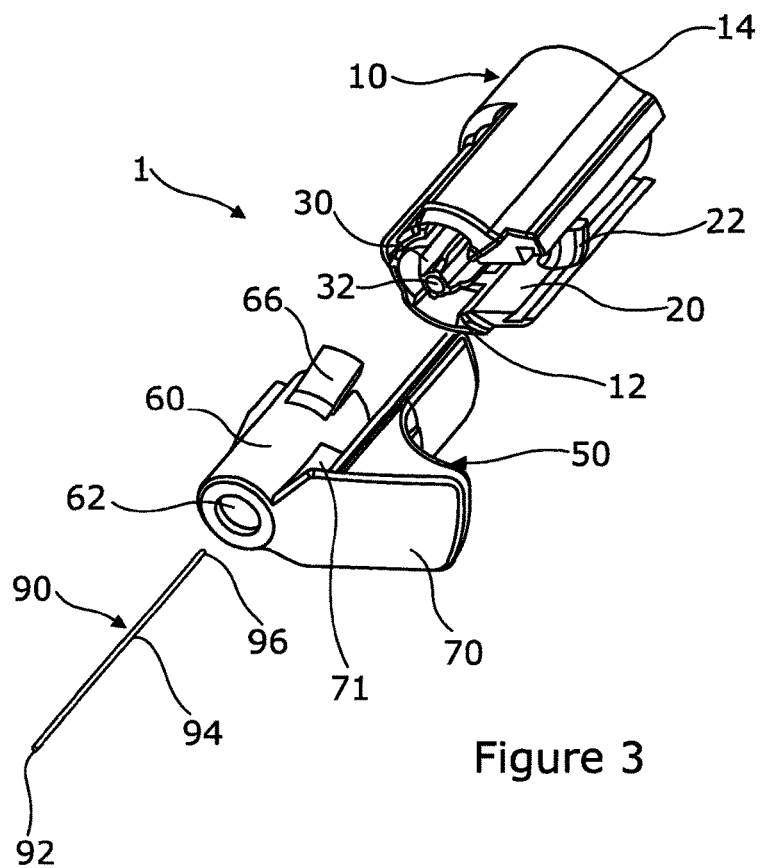

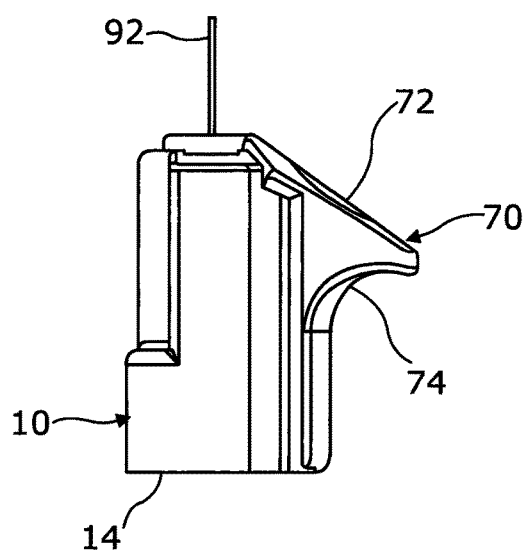
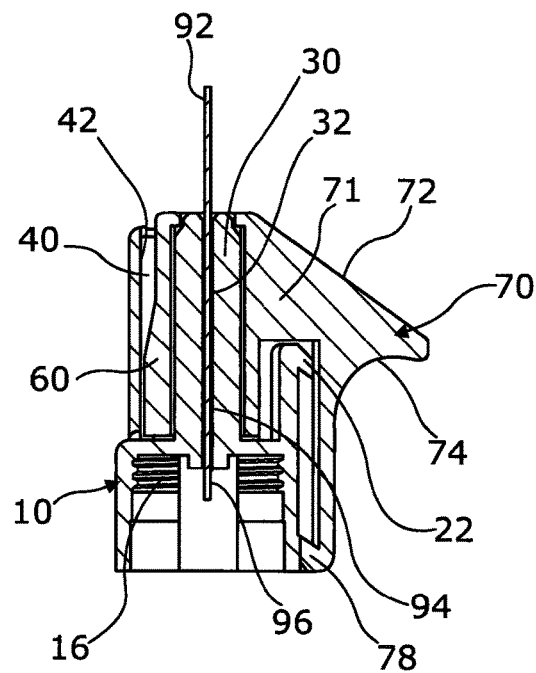
Figure 4A
Figure 4B
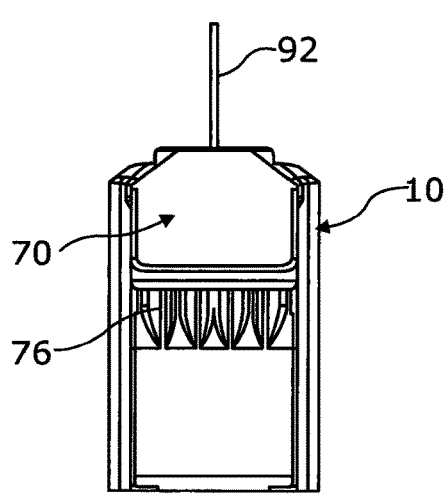
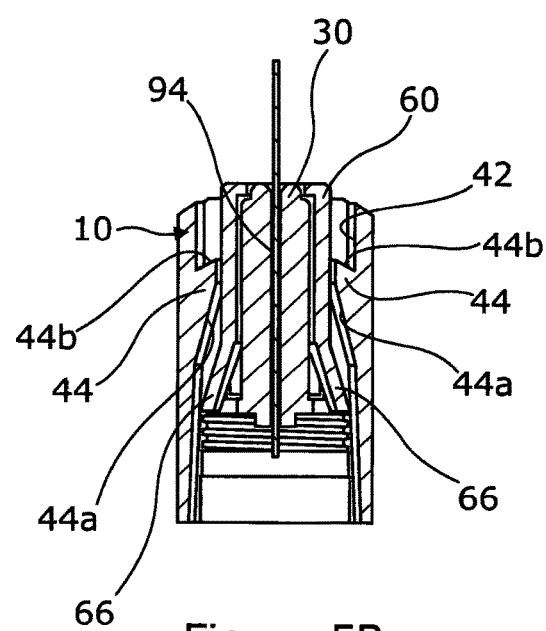
Figure 5A
Figure 5B

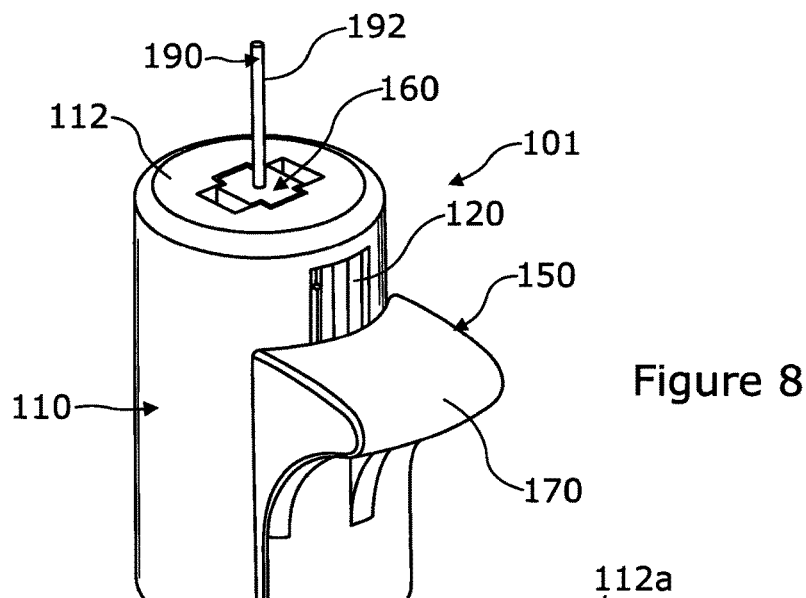
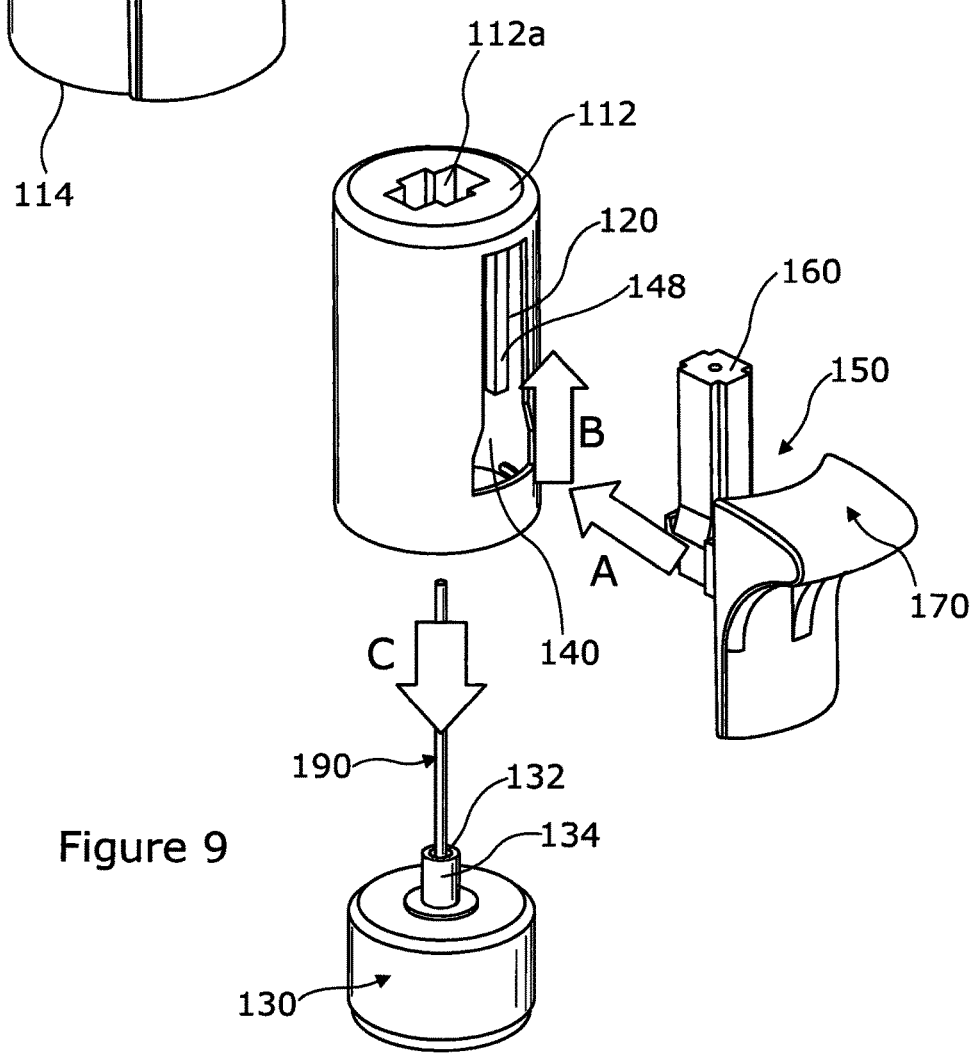

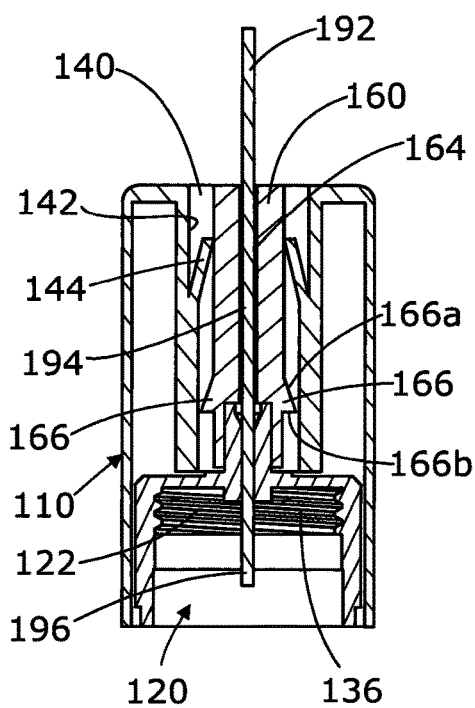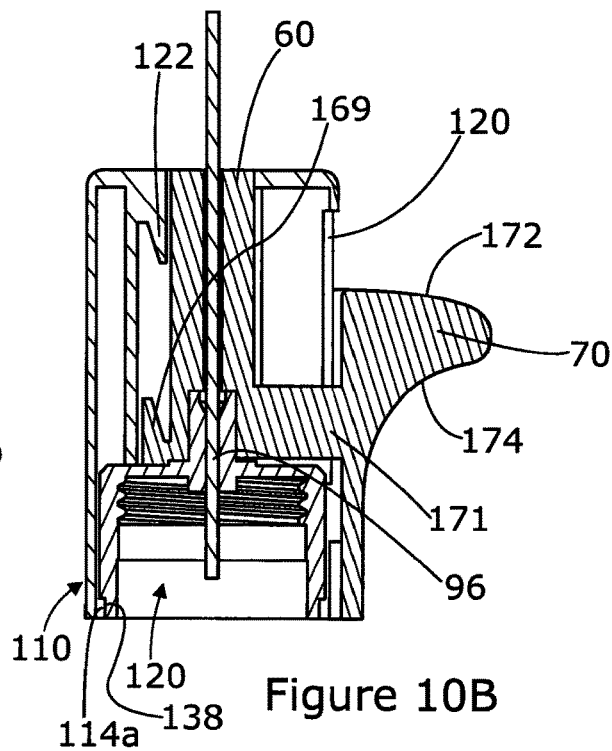
Figure 10A
Figure 10B
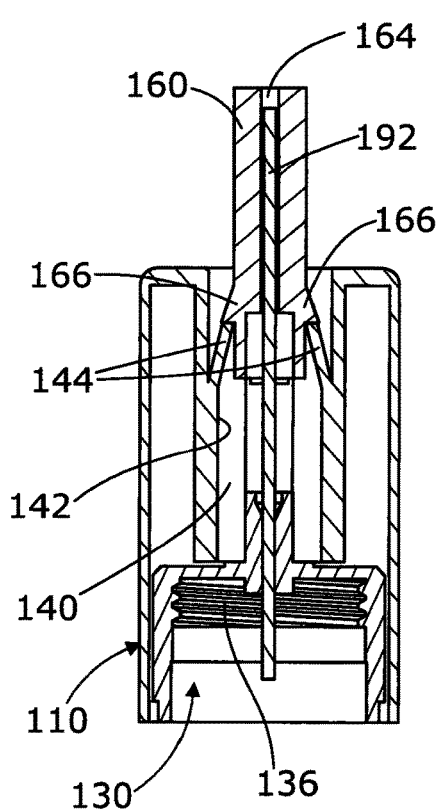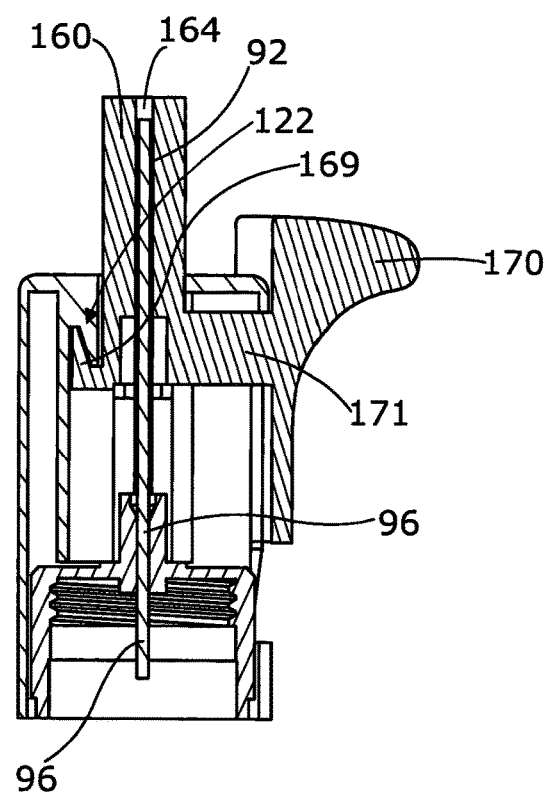
Figure 11A
Figure 11B

NEEDLE ASSEMBLIES

CROSS-REFERENCE TO RELATED APPLICATIONS

This application represents the U.S. National Stage of International Application No. PCT/GB2015/053711 filed Dec. 3, 2015, which is incorporated by reference in its entirety and is based on, claims priority to, and incorporates herein by reference in their entireties, British Patent Application Serial Nos. GB 1421586.7, filed Dec. 4, 2014.

FIELD OF THE INVENTION

This invention relates to needle assemblies for attachment to a syringe or cartridge arrangement or other injection device.

BACKGROUND OF THE INVENTION

There are many situations in which an injection needle is required to be shielded after use to prevent the risk of needle stick injury. This applies not only to single use devices such as disposable syringes and the like, but also to multiple use devices such as cartridges, or pen-type injectors, where a disposable needle is secured, e.g. by screwing or other suitable connection action, into a cartridge or adaptor and replaced for each subsequent injection. Such disposable needles for use with injection devices such as autoinjectors are commonly referred to as "pen needles". The safe shielding of such needles is especially important in clinics and hospitals where the user is injected by a clinician, where the risk of cross-infection is greater.

It is known to provide a removable or detachable shield or protector which is mounted on the forward end of a needle assembly covering the forward tip of the needle. The shield can be removed to carry on the injection and replaced over the needle afterwards. This type of shield can easily get lost or damaged during the injection process. Shields are also known which require the user to grip the medical instrument in one hand and twisting or push an actuator with the other. With either of these arrangements, the user is likely to approach it from the front or side, thus increasing the risk of inadvertent needle stick injury. Further, it is desirable that after a single use, that the needle is not used again, since this increases the risk of cross infection and of tissue damage from blunted needles.

Shield arrangements are also known which are biased towards a position in which the needle is covered such that the needle only projects from the shield during the delivery of the injection with the shield automatically moving back into a shielding position as the needle is removed from the skin. However, such arrangements may add significant complexity and cost to a needle assembly (particularly a single use, disposable needle assembly). Further with such devices the user is generally unable to see the needle during insertion which many users may find disadvantageous.

Embodiments of the invention seek to provide improved needle assemblies which may overcome some or all of these problems.

SUMMARY OF THE INVENTION

Accordingly, in one aspect, this invention provides a needle assembly for mounting on an injection device, comprising:

a main body configured to be removably attached to an injection device in use;
a needle secured in the main body and having a forward portion which projects forwardly from the main body, and
a shield including:
a central portion which is slideably mounted within the main body, the central portion including a cavity for at least partially receiving the needle; and
an actuator portion which extends outside the main body and configured for pushing the shield forward manually in use such that the shield is slideably moveable between
a first position in which the forward portion of the needle projects forwardly of the shield cavity, and
a second position in which said forward portion of the needle is located within the shield cavity; and
wherein the shield and main body are provided with cooperating features comprising at least one latching element provided on one of the shield or the main body and at least one corresponding engagement feature provided on the other of the shield and the main body; wherein the latch moves into a latched position as the shield moves into the second position to hold the shield in its second position.

According to another aspect, the invention provides a needle assembly for mounting on an injection device, comprising:

a main body configured to be removably attached to an injection device in use;
a needle secured in the main body and having a forward portion which projects forwardly from the main body, and
a shield slideably coupled to the main body, the shield including a cavity for at least partially receiving the needle; and
an actuator portion which extends outside the main body and configured for pushing the shield forward manually in use such that the shield is slideably moveable between
a first position in which the forward portion of the needle projects forwardly of the shield cavity, and
a second position in which said forward portion of the needle is located within the shield cavity; and
wherein the shield and main body are provided with cooperating latching features comprising
at least one latching element formed on one of the outer surface of the shield or the inner surface of the main body and
at least one corresponding engagement feature, formed on the other of the outer surface of the shield and the inner surface of the main body, comprising a ramped surface, for resiliently deflecting the corresponding latching element as it moves in a forward direction and a stepped or barbed profile to prevent rearward movement of the corresponding latching element when the shield is in the second position;
wherein the latching element rides over the engagement feature and snaps into a latched position as the shield moves into the second position to hold the shield in its second position.

According to another aspect, the invention provides a needle assembly for mounting on an injection device, comprising:

a main body configured to be removably attached to an injection device in use;
a needle secured in the main body and having a forward portion which projects forwardly from the main body, and
a shield including:
a central portion which is slideably mounted within the main body, the central portion including a cavity for at least partially receiving the needle; and an actuator portion which extends outside the main body;
wherein the shield is slideably moveable between:
a first position in which the forward portion of the needle projects forwardly of the shield cavity, and
a second position in which said forward portion of the needle is located within the shield cavity.

Since the actuator portion is provided outside the main body, it may provide an external manual gripping surface for urging or sliding the shield forward to the second position.

The shield may be manually operable to move it from the first position to the second position.

The shield and the main body may be provided with cooperating features which are configured to engage to hold the shield in its second position.

The cooperating features may be configured to provide an audible and/or tactile indication as they engage. The shield and the main body may make a clicking sound as they engage.

The cooperating features may comprise a latch mechanism which configured to provide an audible and/or tactile indication as the shield moves into the second position.

The cooperating features may comprise at least one latching element provided on one of the shield or the main body. The cooperating features may comprise at least one corresponding engagement feature provided on the other of the shield and the main body. The latch may move into a latched position as the shield moves into the second position.

The at least one latching element may be a resiliently moveable leg. The leg may be arranged to rides over a corresponding engagement feature and snap into a latched position as the shield is moved between the first position and second position. The at least one latching element may be a radially splaying leg (for example an outwardly splaying leg). The at least one latching element may protrude into a bore or chamber provided within the main body.

At least one resiliently moveable leg may be provided on an outer surface of the shield central portion. At least one corresponding engagement feature may be provided on an inner wall of the main body. A plurality of resiliently moveable legs may be provided on an outer surface of the shield central portion. The legs may be equally circumferentially spaced around the shield central portion circumference. A plurality of corresponding engagement features may be provided on an inner wall of the main body. The engagement features may be equally circumferentially spaced around inner wall of the main body At least one resiliently moveable leg may be provided on an inner wall of the main body. At least one corresponding engagement feature may be provided on outer surface of the shield central portion. A plurality of resiliently moveable legs may be provided on an inner wall of the main body, for example the legs may be equally spaced around the inner wall of the main body. A plurality of corresponding engagement features may be provided on an outer surface of the shield central portion, for example the engagement features may be equally spaced around the shield central portion.

The or each engagement feature may include a ramped surface. The ramped surface may be configured for resiliently deflecting the corresponding latching element as it moves in a forward direction. The or each engagement feature may act to hold the shield in its first position when no force is applied to the actuator portion.

The or each engagement feature may include a stepped or barbed profile to prevent rearward movement of the corresponding latching element when the shield is in the second position.

The actuator portion may extend radially outwardly from the main body of the needle assembly. The actuator may provide a rear surface for pushing the shield forward manually in use. The rear surface of the actuator when the shield is in the first position may be provided with a grip surface. The grip surface may include protrusions, a textured surface, or any suitable surface which reduces the risk of a users thumb or finger slipping. The actuator rear surface may be curved, or have any other ergonomically advantageous profile suitable for accommodating a thumb or finger.

The actuator portion may include a substantially forward facing surface. The forward facing surface may include a substantially flat surface, providing a suitable surface on which any required design, for example a product or manufacturer's logo may be printed for otherwise formed. The actuator forward surface may be a sloped surface. The actuator may be radially spaced apart from the shield central portion. The actuator may be connected to the shield central portion at forward end to extend over the outer wall of the main body in the first position. The actuator portion may be connected to the shield central portion by a rib extending substantially radially from the shield central portion.

The outer surface of the main body may be provided with a longitudinally extending slot or groove. The actuator portion may be slideably received in a groove or slot in an outer surface of the main body. The region of the actuator portion adjacent to the shield central portion may be slideably received in a groove in an outer surface.

The shield may be mounted in a bore in the main body. The shield may be mounted in a chamber in the main body, wherein the chamber is defined by the inner surface of the main body walls. The shield and the main body bore (or main body chamber) may have complimentary cross-sectional profiles to prevent relative rotational movement. The shield and the main body bore (or the main body chamber) may have complementary cross-sectional profiles. The cross-sectional profiles may be any convenient geometric shape, such as but not limited to, a key-shape, an oval, a cross, or a square. The main body bore (or the main body chamber) may be provided with protrusions and/or grooves which cooperate with external features on the shield central portion to prevent relative rotational movement.

The main body may be provided with a rear portion. The main body may be provided with a rear portion from which a central core element extends. The central core element may include a needle bore. An intermediate portion of the needle may be secured in the core needle bore, such that a rear portion of the needle extends reawardly from the core needle bore and a forward portion extends forwardly from the core needle bore.

The needle assembly may further comprise at least one stop feature formed between the main body and the shield which blocks forward movement of the shield when the shield reaches the second position. The stop feature may be a protrusion provided on one of the main body and the shield. The protrusion may move into abutment with a feature on the other of the main body and the shield as the shield reaches the second position.

The main body may comprise first and second components, the needle being secured in the first component and the first component being mounted to or in the rear of the second component. For example, the main body may comprise a substantially standard needle fixed in a hub, the hub including a threaded section for connection to the injection device; and a second over moulded or connected component. For example the first component may be a substantially standard pen needle. The second component may for example be formed over or attached to the pen needle in an additional manufacturing step. The first body component may comprise a connection mechanism for connecting the needle assembly to a syringe, cartridge or other injection device. The first (rear) body component may be mounted to or on the rear of the second (forward) body component. The first body component may be mounted inside the second body component. The second body component may have a rearwardly facing recess or cavity; and a bore or cavity extending forwardly from the recess to the forward surface of second body component. The first body component may be mounted in the recess of the second body component.

The first body component may include a needle bore. The second body component may include a needle bore which aligns with the needle bore in the first body component when the two components are assembled.

The needle may be mounted in or secured to the second body component, such that when the second body component is mounted in or to the first body component, the forward end of needle extends forwardly through the first body component. The second body component may be releasably mounted in or to the first body component. The second body component may be non-removably secured in or to the first body component, for example by gluing.

The shield and/or main body may be formed from a suitable plastic material, typically a polymer, such as but not limited to propylene.

The needle may double ended with a rear portion opposite the forward portion. The rear end of the rear portion may be configured in use for piercing a seal element. Such an arrangement may be used in a needle to be attached to an injection device (such as an autoinjector) as the rear needle portion may be configured to pierce the septum of a cartridge or syringe when attached to the injection device.

The needle assembly may further comprise a removable protector which shields or covers the forward portion of the needle. The removable protector may also shield or cover at least a part of the forward portion of the main body. The removable connector may provide a sterile seal to the needle assembly prior to use.

The rear portion of the main body may comprise a connection mechanism for connecting the needle assembly to a syringe, cartridge or other injection device. The connection mechanism may be a threaded portion, bayonet fitting or any other suitable engagement element which corresponds to the engagement element on the injection device.

The rear portion of the main body may be configured to be attached to standard hubs or other components provided on the front of syringes, cartridge arrangements or other injection devices. This means that the needle assembly can be attached to any of a range of standard injection devices.

The needle assembly may be mounted or attached to the forward end of an injection device, by screwing or other suitable connection action.

The needle assembly of the invention is a disposable, single-use, needle assembly for use with an injection device. The injection device may be a multi-use or reusable device. In a multi-use injection device, the syringe/cartridge may be replaceable or disposable, and/or arranged to deliver a plurality of doses.

The needle assembly may be a pen needle assembly for use with a pen-type injector.

To assemble the needle assembly, the shield central portion may be inserted vertically into a bore or chamber in the main body from a forward end of the main body. Alternatively, the shield central portion may be inserted horizontally into the main body through a slot provided in the side of the main body.

The needle may be vertically mounted into the main body, along the longitudinal needle axis and secured in position, for example by gluing. If the main body includes two components, the needle may be vertically assembled or mounted into the first (rear) body component and secured against longitudinal movement, for example by gluing. The first (rear) body component may be vertically mounted into and secured in the rear recess of the second (forward) body component.

Whilst the invention has been described above, it extends to any inventive combination of the features set out above or in the following description or drawings.

BRIEF DESCRIPTION OF THE DRAWINGS

FIG. 1 shows a first needle assembly in accordance with an embodiment of the invention in a first, operable configuration, which is the configuration of the assembly before and during injection, with the shield in a first position;

FIG. 2 shows a perspective view of the first needle assembly in a second safe configuration with the shield in a second position;

FIG. 3 shows a perspective exploded view of the needle assembly of FIG. 1;

FIGS. 4A and 4B show a side view of the needle assembly of FIG. 1 and a cross-sectional view;

FIGS. 5A and 5B show an end view and a cross-sectional view of the needle assembly of FIG. 1;

FIG. 8 shows a perspective view of a second needle assembly in accordance with another embodiment of the invention, in a first, operable configuration, which is the configuration of the assembly before and during injection, with the shield in a first position;

FIG. 9 shows a perspective exploded view of the needle assembly of FIG. 8;

FIGS. 10A and 10B show a side view and a cross-sectional view of the needle assembly of FIG. 8; and FIGS. 11A and 11B show a side view and a cross-sectional view of the second needle assembly second safe configuration with the shield in a second position The embodiments illustrated in the Figures are needle assemblies intended to be screwed or otherwise attached to the forward end of a syringe, cartridge or injection device such as a "pen-type" injector, to allow injection of a substance.

DESCRIPTION OF AN EMBODIMENT

Figure 6A:
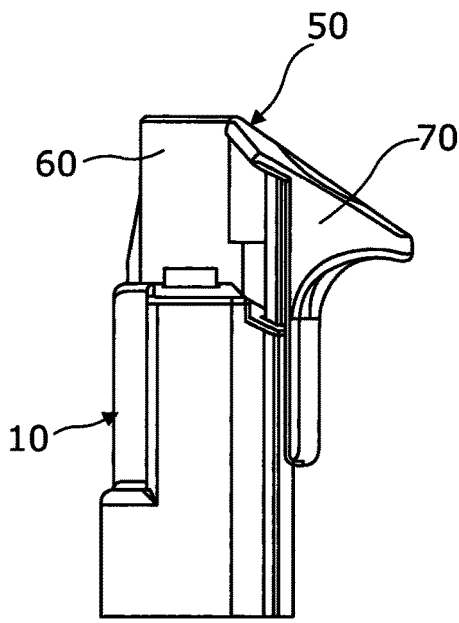
FIGS. 6A and 6B show a side view and a cross-sectional view of the needle assembly of FIG. 2.

In the following embodiments, the terms "forward" and "front" refer to the patient end of the needle assembly or component thereof, and the term "rear" refers to the non-patient end of the needle assembly or component thereof. In other words, the term "rear" means distant or remote from the injection site during use.

FIG. 1 shows a needle assembly 1 in a first configuration, which is the configuration of the assembly before and during injection. FIG. 2 shows the needle assembly 1 in a second configuration. The needle assembly 1 includes a main body 10, a shield 50 and a needle 90.

The main body 10 is substantially cylindrical and includes a front portion 12 and a rear portion 14. The front portion 12 has an internal cavity or chamber 40 which is open at a forward end. The rear portion 14 includes a rear cavity with a threaded portion 16 (FIG. 4B) for attaching the needle assembly 1 to the front end of a syringe, cartridge or other injection device (not shown).

The main body 10 is provided with a longitudinally extending slot 20 in the external wall of the front portion 12. The slot 20 extends from the front surface of the main body 10 in a rearward direction. An outwardly projecting stop feature 22 is provided at the distal end of the slot 20.

The main body 10 also includes an inner core 30 which is located centrally in the chamber 40 having an inner wall 42. The inner core 30 spaced from and integral with the inner wall 42 of the front portion 12. The inner core 30 has a needle bore 32 extending through it (FIG. 3). The needle 90 extends longitudinally along a needle axis. An intermediate portion 96 of the needle 90 is secured in the core needle bore 32; a forward end 92 of the needle extends forwardly from the needle bore 32 and a rear end 94 of the needle extends rearwardly in the main body rear portion 14 (FIG. 4B).

The shield 50 includes a central portion 60 and an actuator portion 70. The central portion 60 has a substantially cylindrical form with a front surface defining an opening 62. The central portion 60 has an internal cavity or chamber 64 which is open at a forward end via the opening 62 and is also open at a rear end. The actuator portion 70 extends radially from the central portion 60 and it is formed integrally with the central portion 60. The outer surface of the central portion 60 is provided with two latching elements in the form of resiliently deformable legs 66, which are splayed outwardly. The legs 66 are resiliently biased outwards. The legs 66 are equally spaced around the circumference of the central portion 60.

The actuator portion 70 includes a rib 71 extending from the outer surface of the central portion 60 (FIGS. 4A and 4B). The rib 71 is provided with a forward facing surface 72 and a rear facing surface 74. The two surfaces 72, 74 meet at a point distal from the central portion. The actuator portion 70 is provided with an ergonomic profile to make the actuation easier for the user. For example, the rear surface 74 may have a curved profile to accommodate the users thumb or finger (as shown in the Figures), with a gripping surface 76 to prevent slipping. The gripping surface 76 includes projections or may be a textured surface. The rear surface 74 is therefore clearly distinguishable as the surface on which the user pushes to move the shield 50. The rear end of the actuator is provided with an inward protrusion 78.

The forward facing surface 72 is a substantially flat surface, on which any required design, for example a product or manufacturer's logo or other information may be printed for otherwise formed (FIGS. 3 and 4A).

In other embodiments (not shown), the shape and configuration of the forward and rear facing surfaces of the actuator portion vary.

The main body chamber inner walls 42 are provided with engagement features, in the form of protrusions 44, which extend inwardly into the chamber 40 (FIG. 5A). In this embodiment two protrusions 44 are provided to cooperate with the two resilient legs 66 on the shield central portion 60. The protrusions 44 have a rear facing surface 44a and a forward surface 44b. The rear surface 44a has a sloped surface, or ramped surface, extending inwards from the inner wall 42 for resiliently deflecting the corresponding resilient leg 66 as it moves in a forward direction from the position in FIG. 5A to that in FIG. 7A. The forward face 44b is formed with a stepped or barbed profile to prevent rearward movement of the corresponding leg when the shield is in the second position (FIG. 7A).

As shown in FIG. 3, the shield 50 is mounted to the main body 10 from the forward end. In order to mount the shield 50 in the body, an assembly tool is required to deflect the legs 66 inwards so that they do not impact against the protrusions 44 provided on the inner wall 42 of the main body chamber 40.

The second configuration of the needle assembly 1 is shown in FIGS. 2 and 6A to 7B. In the second configuration, the shield 50 is in its second or forward position and the forward portion of the needle 92 is located within the shield central portion cavity 64. This means that there is no risk of the user injuring themselves on the needle when the needle assembly is in this configuration.

Figure 6B:
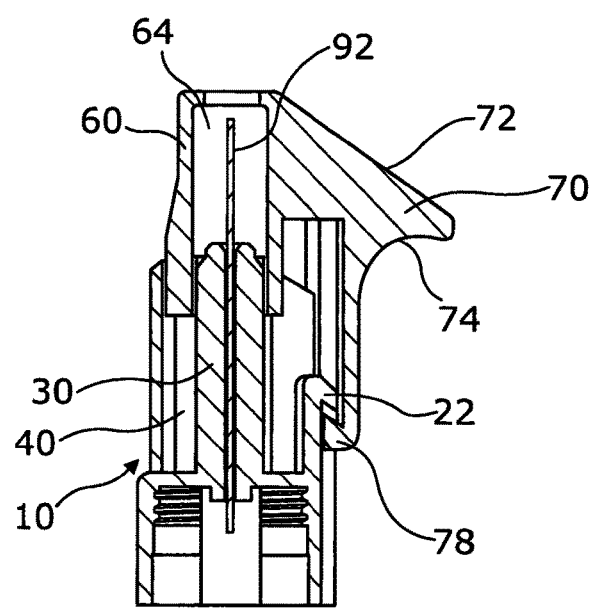
Figure 7A:
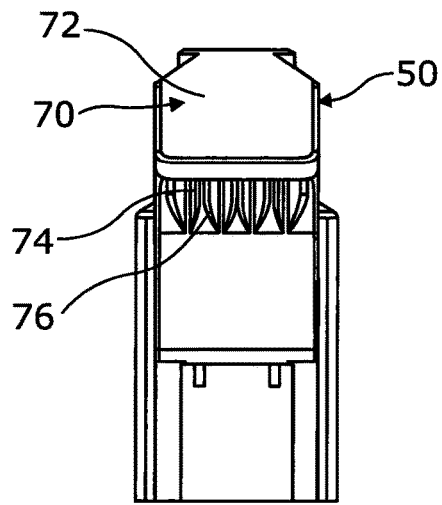
FIGS. 7A and 7B show an end view and a cross-sectional view of the needle assembly of FIG. 2.
Figure 7B:
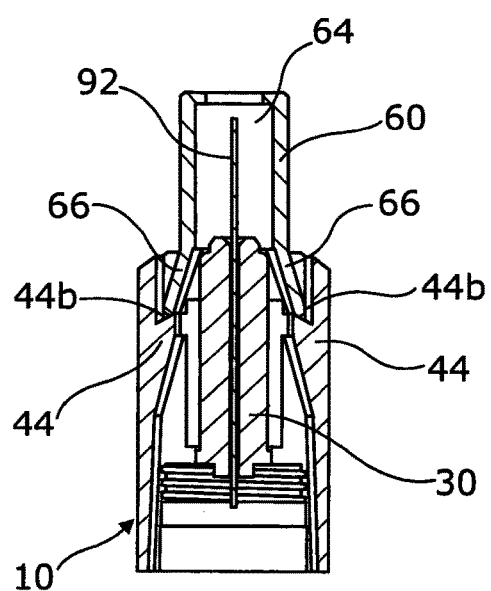

In this configuration, the resilient legs 66 are engaged with the forward surface 44b of the protrusion 44 (FIG. 7A). Due to the stepped or barbed profile of the forward surface 44b, the legs are locked in this position and the shield is no longer able to move rearwardly. As shown in FIG. 6B, the stop feature 22 on the main body 10 is engaged with the inward protrusion 78 on the actuator which prevents the shield from moving further forward and stops the shield from being pushed forwardly away from the main body 10. This means that the needle assembly is locked in the second, safe configuration.

In other embodiments (not shown), a different number of legs and protrusions are provided. In one embodiment (not shown), a single resilient leg is provided on the shield central portion, and a single protrusion is provided on the chamber inner wall 42.

In yet other embodiments (not shown), the resilient leg(s) is provided on the chamber inner wall and the protrusion(s) is provided on the shield central portion.

FIG. 8 shows a second needle assembly 101 in a first configuration, which is the configuration of the assembly before and during injection. As can be seen from the exploded view in FIG. 9, the needle assembly 101 (FIG. 9) includes a main body 110, a rear body 130; a shield 150 and a needle 190.

The main body 110 is substantially cylindrical and includes a front portion 112 and a rear portion 114. An opening 112a is provided on a forward surface of the front portion 112. The front portion 112 has an internal cavity or chamber 140 which partially open at a forward end. The internal chamber 140 is defined by an inner wall 142. Provided on the inner wall 142 are latching elements in the form of resiliently deformable legs 144, which are splayed outwardly from the surface of the wall. The legs are resiliently biased outwards. The legs 144 are equally spaced around the circumference of the inner wall 142. A stop feature 122 is provided at a forward end of the chamber 140 (FIG. 10B). The stop feature 122 is circumferentially spaced from both the legs 144, and in this embodiment the stop feature is provided substantially midway between the two legs in a circumferential direction. The stop feature 122 comprises a rearwardly extending protrusion having a sloped profile on a surface adjacent to the inner wall 142.

The main body rear portion 114 includes a rear cavity in which a rear body portion 130 is inserted. The rear body portion 130 includes a rear cavity with a threaded portion 136 (FIG. 10A) for attaching the needle assembly 101 to the front end of a syringe, cartridge or other injection device (not shown). The rear body 130 includes a central forward element 134 having a needle bore 132 which extends through the central element, rearwardly to the rear cavity of the rear portion (FIGS. 9 and 10A). The rear body portion 130 is provided with a first engagement feature 138 which engages with a corresponding feature 114a on the main body to securely couple the two components.

The main body 110 is provided with a longitudinally extending slot 120 in an external wall.

The shield 150 includes a central portion 160 and an actuator portion 170. The central portion 160 extends longitudinally and includes a needle bore 164. The actuator portion 170 extends radially from the central portion 160 and it is formed integrally with the central portion 160.

The central portion 160 includes a protrusion 178 at a rear end which extends outwardly (FIG. 10B). The protrusion 178 has a forward facing surface with a barbed profile (FIG. 10B). When the shield is moved into the second position (FIG. 11B), the protrusion engages with the stop feature 122 in the main body chamber 140.

The outer surface of the central portion 160 is provided with engagement features, in the form of protrusions 166, which extend outwardly from the central portion outer surface 160. When the central portion 160 is mounted in the main body portion 110, the protrusions 166 extend outwardly into the chamber 140 (FIG. 10A). In this embodiment two protrusions 166 are provided to cooperate with the two resilient legs 166 on the chamber inner wall 142. The protrusions 166 have a forward facing surface 166a and a rear surface 166b. The forward surface 166a has a sloped surface, or ramped surface, extending outwards from the central portion for resiliently deflecting the corresponding resilient leg 144 as it moves in a forward direction from the position in FIG. 10A to that in FIG. 11A. The rear face 166b is formed with a stepped or barbed profile to prevent rearward movement of the corresponding leg when the shield is in the second position (FIG. 11A).

The actuator portion 170 includes a rib 171 extending from the outer surface of the central portion 160 (FIGS. 9 and 10B). The rib 171 is provided with a forward facing surface 172 and a rear facing surface 174. The two surfaces 172, 174 meet at a point distal from the central portion. As with the previous embodiment, the actuator portion 170 is provided with an ergonomic profile to make the actuation easier for the user. In the embodiment shown, the rear surface 174 has a curved profile to accommodate the users thumb or finger (as shown in the Figures), with a gripping surface 176 to prevent slipping. The forward facing surface 172 is a substantially flat surface, on which any required design, for example a product or manufacturer's logo may be printed for otherwise formed (FIG. 9).

The shield central portion 160 and the main body chamber 140 have complimentary cross-sectional profiles to prevent relative rotational movement. In this embodiment, the shield central portion 160 has a cross sectional profile in the form of a cross (FIG. 9). The main body chamber 140 is provided with inwardly projecting ribs (which can be seen through the slot 120 and the opening 112a in FIG. 9), which cooperate with the external features of the shield central portion 160 when it is mounted in the chamber 140. The forward opening 112a has a corresponding cross-shape (FIG. 9), through which the shield central portion passes as the shield is moved from the first position to the second position.

As shown in FIG. 9, the shield 150 is mounted or assembled to the main body 110 from the side of the main body through the slot 120, as shown by arrow A. The shield 150 is then moved into the first position, as shown by arrow B. The intermediate portion of the needle 96 is secured in the rear body portion 130, as shown by arrow C. The rear body portion 130 is then mounted into the rear recess of the main body 110.

The second configuration of the needle assembly 101 is shown in FIGS. 11A and B. In the second configuration, the shield 150 is in its second or forward position and the forward portion of the needle 192 is located within the shield central portion bore 164.

In this configuration, the resilient legs 144 are engaged with the rear surface 166b of the protrusion 166 (FIG. 11A). Due to the stepped or barbed profile of the surface 166b, the legs are locked in this position and the shield 150 is no longer able to move rearwardly. As shown in FIG. 11B, the rib 171 engages on the forward edge of the slot 120, and the stop feature 122 on the main body 110 is engaged with the protrusion 178 on the actuator. This prevents the shield 150 from moving further forward in the main body 110. This means that the needle assembly 101 is locked in the second, safe configuration.

In other embodiments (not shown), a different number of legs and protrusions are provided. In one embodiment (not shown), a single resilient leg is provided on the inner wall, and a single protrusion is provided on the shield central portion.

In yet other embodiments (not shown), the protrusion(s) is provided on the chamber inner wall and the resilient leg(s) is provided on the shield central portion In embodiments of the invention, the needle assembly components are moulded plastic components. The configuration of the invention is simple and easy to manufacture and assemble, which means the cost is low. This is important for single use or disposable needle assemblies.

In all embodiments of the invention, the needle assembly may also be provided with needle cover or sheath (not shown) which covers the forward end of the needle prior to use. The needle assembly is provided ready for use with the needle cover mounted over the forward end of the needle. This protects the user from needle-stick injury when attaching the needle assembly to the injection device.

The needle assembly may also be provided with a further indicator (not shown) which provides at least one of a tactile, an audible and a visual indication that the shield is secured to the main body.

The invention claimed is:

1. A needle assembly for mounting on an injection device, comprising:
   a main body configured to be removably attached to an injection device in use;
   a needle secured in the main body and having a forward portion which projects forwardly from the main body, and
   a shield including:
      a central portion which is slideably mounted within the main body, the central portion including a cavity for at least partially receiving the needle; and
      an actuator portion which extends outside the main body and configured for pushing the shield forward manually in use such that the shield is slideably moveable between
      a first position in which the forward portion of the needle projects forwardly of the shield cavity, and
      a second position in which said forward portion of the needle is located within the shield cavity; and
   wherein the shield and main body are provided with cooperating features comprising at least one latching element having a resiliently movable leg provided on one of the shield or the main body and at least one corresponding engagement feature provided on the other of the shield and the main body; comprising a ramped surface, for resiliently deflecting the corresponding latching element as the shield moves in a forward direction and a stepped or barbed profile to prevent rearward movement of the shield relative to the main body when the shield is in the second position, wherein the latching element rides over the engagement feature and snaps into a latched position as the shield moves into the second position to hold the shield in its second position, and wherein the actuator is radially spaced apart from the shield central portion and connected at a forward end to extend over the outer wall of the main body in the first position.

2. A needle assembly for mounting on an injection device, comprising:

a main body configured to be removably attached to an injection device in use;

a needle secured in the main body and having a forward portion which projects forwardly from the main body, and a shield slideably coupled to the main body, the shield including a cavity for at least partially receiving the needle; and an actuator portion which extends outside the main body and configured for pushing the shield forward manually in use such that the shield is slideably moveable between a first position in which the forward portion of the needle projects forwardly of the shield cavity, and a second position in which said forward portion of the needle is located within the shield cavity; and wherein the shield and main body are provided with cooperating latching features comprising at least one latching element formed on one of the outer surface of the shield or the inner surface of the main body and at least one corresponding engagement feature, formed on the other of the outer surface of the shield and the inner surface of the main body, comprising a ramped surface, for resiliently deflecting the corresponding latching element as it moves in a forward direction and a stepped or barbed profile to prevent rearward movement of the corresponding latching element when the shield is in the second position;

wherein the latching element rides over the engagement feature and snaps into a latched position as the shield moves into the second position to hold the shield in its second position, and wherein the actuator is radially spaced apart from the shield central portion and connected at forward end to extend over the outer wall of the main body in the first position.

3. A needle assembly according to claim 1 or claim 2, wherein the cooperating features are formed on an inner surface of the main body and an outer surface of the shield.

4. A needle assembly according to claim 1 or claim 2, wherein the at least one latching element is a resiliently moveable leg which rides over a corresponding engagement feature and snaps into a latched position as the shield is moved between the first and second position.

5. A needle assembly according to claim 4, wherein at least one resiliently moveable leg is provided on an outer surface of the shield central portion; and at least one corresponding engagement feature is provided on an inner wall of the main body.

6. A needle assembly according to claim 1 or claim 2, wherein the actuator portion extends radially outwardly from the main body of the needle assembly and provides a rear surface for pushing the shield forward manually in use.

7. A needle assembly according to claim 1 or claim 2, wherein the actuator portion is slideably received in a groove or slot in an outer surface of the main body.

8. A needle assembly according to claim 1 or claim 2, wherein the cooperating features are configured to provide an audible and/or tactile indication as they engage.

9. A needle assembly according to claim 1 or claim 2, wherein the shield is mounted in a bore in the main body, wherein the shield and the main body bore have complimentary cross-sectional profiles to prevent relative rotational movement.

10. A needle assembly according to claim 1 or claim 2, further comprising a stop feature formed between the main body and the shield which blocks forward movement of the shield when the shield reaches the second position.

11. A needle assembly according to claim 1 or claim 2, wherein the main body comprises first and second components, the needle being secured in the first component and the first component being mounted to or in the rear of the second component.

12. An injection device including a needle assembly according to claim 1 or claim 2 mounted to its forward end.

13. A needle assembly for mounting on an injection device, comprising:

a main body configured to be removably attached to an injection device in use;

a needle secured in the main body and having a forward portion which projects forwardly from the main body, and a shield including:

a central portion which is slideably coupled to the main body, the central portion including a cavity for at least partially receiving the needle; and an actuator portion which extends outside the main body and is configured for pushing the shield forward manually in use such that the shield is slideably moveable between a first position in which the forward portion of the needle projects forwardly of the shield cavity, and a second position in which said forward portion of the needle is located within the shield cavity; and wherein the shield and main body are provided with cooperating features comprising at least one latching element having a resiliently movable leg provided on one of the shield or the main body;

at least one corresponding engagement feature provided on the other of the shield and the main body comprising a ramped surface on a forward end of the engagement feature, for resiliently deflecting the corresponding latching element as the shield moves in a forward direction and a stepped profile to prevent rearward movement of the shield relative to the main body when the shield is in the second position, and a cylindrical opening on the forward end of the shield, wherein the latching element rides over the engagement feature and snaps into a latched position as the shield moves into the second position to hold the shield in its second position, and wherein the actuator is radially spaced apart from the shield central portion and connected at a forward end to extend over the outer wall of the main body in the first position.

* * * * *